US006506154B1

(12) United States Patent
Ezion et al.

(10) Patent No.: US 6,506,154 B1
(45) Date of Patent: Jan. 14, 2003

(54) SYSTEMS AND METHODS FOR CONTROLLING A PHASED ARRAY FOCUSED ULTRASOUND SYSTEM

(75) Inventors: Avner Ezion, Haifa (IL); Kolisher Izzydor, K. Motzkin (IL); Shuki Vitek, Haifa (IL)

(73) Assignee: InSightec-TxSonics, Ltd., Tirat Carmel (IL)

( * ) Notice: Subject to any disclaimer, the term of this patent is extended or adjusted under 35 U.S.C. 154(b) by 72 days.

(21) Appl. No.: 09/724,611

(22) Filed: Nov. 28, 2000

(51) Int. Cl.[7] ................................................ A61B 8/00
(52) U.S. Cl. ...................................................... 600/437
(58) Field of Search ................................ 600/407, 437, 600/439–447, 459; 367/7, 11, 138, 103

(56) References Cited

U.S. PATENT DOCUMENTS

| | | | | |
|---|---|---|---|---|
| 4,616,231 A | | 10/1986 | Autrey et al. | 342/374 |
| 4,823,053 A | | 4/1989 | McCracken | 318/132 |
| 4,865,042 A | | 9/1989 | Umemura et al. | 128/334 |
| 5,165,412 A | * | 11/1992 | Okazaki | 600/439 |
| 5,172,343 A | * | 12/1992 | O'Donnell | 367/103 |
| 5,269,307 A | | 12/1993 | Fife et al. | 128/661.01 |
| 5,329,930 A | * | 7/1994 | Thomas et al. | 600/443 |
| 5,388,461 A | * | 2/1995 | Rigby | 600/442 |
| 5,590,657 A | * | 1/1997 | Cain et al. | 600/439 |
| 6,128,958 A | * | 10/2000 | Cain | 367/138 |

FOREIGN PATENT DOCUMENTS

| | | | |
|---|---|---|---|
| WO | WO 01/80708 A3 | 1/2001 | A61B/8/00 |
| WO | WO 01/80708 A2 | 1/2001 | |

* cited by examiner

*Primary Examiner*—Marvin M. Lateef
*Assistant Examiner*—Ali M. Imam
(74) *Attorney, Agent, or Firm*—Bingham McCutchen LLP

(57) ABSTRACT

Systems and methods for controlling the phase and amplitude of individual drive sinus waves of a phased-array focused ultrasound transducer employ digitally controlled components to scale the amplitude of three or more bases sinuses into component sinus vectors. The component sinus vectors are linearly combined to generate the respective sinus of a selected phase and amplitude. The use of digitally controlled controlled components allows for digitally controlled switching between various distances, shapes and orientations ("characteristics") of the focal zone of the transducer. The respective input parameters for any number of possible focal zone characteristics may be stored in a comprehensive table or memory for readily switching between focal zone characteristics in $\mu$ seconds. Changes in the output frequency are accomplished without impacting on the specific focal zone characteristics of the transducer output. Sequential changes in the transducer focal zone characteristics are implemented in the form of sequential sets of digital control signals transmitted from the central controller to respective control channels for generating the individual sinus waves. The digital control signals may be changed in accordance with a time-domain function as part of a single thermal dose.

25 Claims, 6 Drawing Sheets

SYSTEMS AND METHODS FOR CONTROLLING A PHASED ARRAY FOCUSED ULTRASOUND SYSTEM

FIELD OF THE INVENTION

The present invention relates generally to focused ultrasound systems and, more particularly, to systems and methods for controlling a phased array transducer in a focused ultrasound system in order to focus acoustic energy transmitted by respective transducer elements at one or more target focal zones in a patient's body.

BACKGROUND

High intensity focused acoustic waves, such as ultrasonic waves (i.e., with a frequency greater than about 20 kilohertz), may be used to therapeutically treat internal tissue regions within a patient. For example, ultrasonic waves may be used to ablate tumors, eliminating the need for invasive surgery. For this purpose, focused ultrasound systems having piezoelectric transducers driven by electric signals to produce ultrasonic energy have been employed.

In systems, such as a focused ultrasound system, the transducer is positioned external to the patient, but in generally close proximity to a target tissue region within the patient to be ablated. The transducer may be geometrically shaped and positioned so that the ultrasonic energy is focused at a "focal zone" corresponding to the target tissue region, heating the region until the tissue is necrosed. The transducer may be sequentially focused and activated at a number of focal zones in close proximity to one another. For example, this series of "sonications" may be used to cause coagulation necrosis of an entire tissue structure, such as a tumor, of a desired size and shape.

By way of illustration, FIG. 1 depicts a phased array transducer 10 having a "spherical cap" shape. The transducer 10 includes a plurality of concentric rings 12 disposed on a curved surface having a radius of curvature defining a portion of a sphere. The concentric rings 12 generally have equal surface areas and may also be divided circumferentially 14 into a plurality of curved transducer sectors, or elements 16, creating a "tiling" of the face of the transducer 10. The transducer elements 16 are constructed of a piezoelectric material such that, upon being driven with a sinus wave near the resonant frequency of the piezoelectric material, the elements 16 vibrate according to the phase and amplitude of the exciting sinus wave, thereby creating the desired ultrasonic wave energy.

As illustrated in FIG. 2, the relative phase shift and amplitude of the sinus drive signal for each transducer element 16 is individually controlled so as to sum the emitted ultrasonic wave energy 18 at a focal zone 13 having a desired focused planar and volumetric pattern. This is accomplished by coordinating the signal phase of the respective transducer elements 16 in such a manner that they constructively interfere at specific locations, and destructively cancel at other locations. For example, if each of the elements 16 are driven with drive signals that are in phase with one another, (known as "mode 0"), the emitted ultrasonic wave energy 18 are focused at a relatively narrow focal zone. Alternatively, the elements 16 may be driven with respective drive signals that are in a predetermined shifted-phase relationship with one another (referred to in U.S. Pat. No. 4,865,042 to Umemura et al. as "mode n"). This results in a focal zone that includes a plurality of 2n zones disposed about an annulus, i.e., generally defining an annular shape, creating a wider focus that causes necrosis of a larger tissue region within a focal plane intersecting the focal zone. Various distances, shapes and orientations (relative to an axis of symmetry) of the focal zone can be created by controlling the relative phases and amplitudes of the emitted energy waves from the transducer array, including steering and scanning of the beam, thereby enabling electronic control of the focused beam to cover and treat multiple spots in a target tissue area (e.g., a defined tumor) inside the patient's body.

More advanced techniques for obtaining specific focal zone characteristics are disclosed in U.S. patent application Ser. No. 09/626,176, filed Jul. 27, 2000, entitled "Systems and Methods for Controlling Distribution of Acoustic Energy Around a Focal Point Using a Focused Ultrasound System;" U.S. patent application Ser. No. 09/556,095, filed Apr. 21, 2000, entitled "Systems and Methods for Reducing Secondary Hot Spots in a Phased Array Focused Ultrasound System;" and U.S. patent application Ser. No. 09/557,078, filed Apr. 21, 2000, entitled "Systems and Methods for Creating Longer Necrosed Volumes Using a Phased Array Focused Ultrasound System." The foregoing patent applications, along with U.S. Pat. No. 4,865,042, are all hereby incorporated by reference for all they teach and disclose.

It is significant to implementing these focal zone positioning and shaping techniques to provide a transducer control system that allows the phase of each transducer element to be independently controlled. To provide for precise positioning and dynamic movement and reshaping of the focal zone, it is desirable to be able to alter the phase and/or amplitude of the individual elements relatively fast, e.g., in they second range, to allow switching between focal zone characteristics or modes of operation. As taught in the above-incorporated U.S. patent application Ser. No. 09/556,095, it may also be desirable to be able to rapidly change the drive signal frequency of one or more elements. In a MRI-guided focused ultrasound system, it is desirable to be able to drive the ultrasound transducer array without creating electrical harmonics, noise, or fields that interfere with the ultra-sensitive receiver signals that create the images.

Thus, it is desirable to provide a system and methods for individually controlling, and dynamically changing, the driving voltage, phase and amplitude of each transducer element in phased array focused ultrasound transducer a manner that does not interfere with the imaging system.

SUMMARY OF THE INVENTION

The present invention provides systems and methods for controlling the phase and amplitude of individual drive sinus waves of a phased-array focused ultrasound transducer. In one embodiment, digital potentiometers are used to scale the amplitude of a selected two of four orthogonal bases sinuses having respective phases of 0°, 90°, 180°, and 270° into component sinus vectors. The component sinus vectors are linearly combined to generate the respective sinus of a selected phase and amplitude. The use of digitally controlled potentiometers allows for digitally controlled switching between various focal zone characteristics. For example, the respective input parameters for any number of possible focal zone distances, shapes and orientations may be stored in a comprehensive table or memory for readily switching between the various focal zone characteristics in $\mu$ seconds.

In a preferred embodiment, changes in the output frequency are also readily accomplished without impacting on the specific focal zone characteristics of the transducer output. Towards this end, sequential changes in the distance, shape and/or orientation of the focal zone are implemented in the form of sequential sets of digital control signals (or "sonication parameters") transmitted from the central controller to respective control channels for generating the individual sinus waves. The digital control signals may be changed in accordance with a time-domain function as part of a single thermal dose, or "sonication." In other words, during a single sonication, the systems and methods provided herein allow for switching between ultrasound energy beam focal shapes and locations at a rate that is relatively high compared to the heat transfer time constant in a patient's tissue.

In accordance with a further aspect of the invention, each set of sonication input parameters has a corresponding set of expected, or planned, output phase and amplitude levels for each sinus wave. The actual output levels are then measured and if either of the actual phase or amplitude differs from what is expected for the respective sinus wave, the particular drive sinus wave, or perhaps the entire system, may be shut down as a precautionary safety measure.

Other objects and features of the present invention will become apparent from consideration of the following description taken in conjunction with the accompanying drawings.

BRIEF DESCRIPTION OF THE DRAWINGS

Preferred embodiments of the present invention are illustrated by way of example, and not by way of limitation, in the figures of the accompanying drawings, in which.

DETAILED DESCRIPTION OF THE PREFERRED EMBODIMENTS

Figure 1:
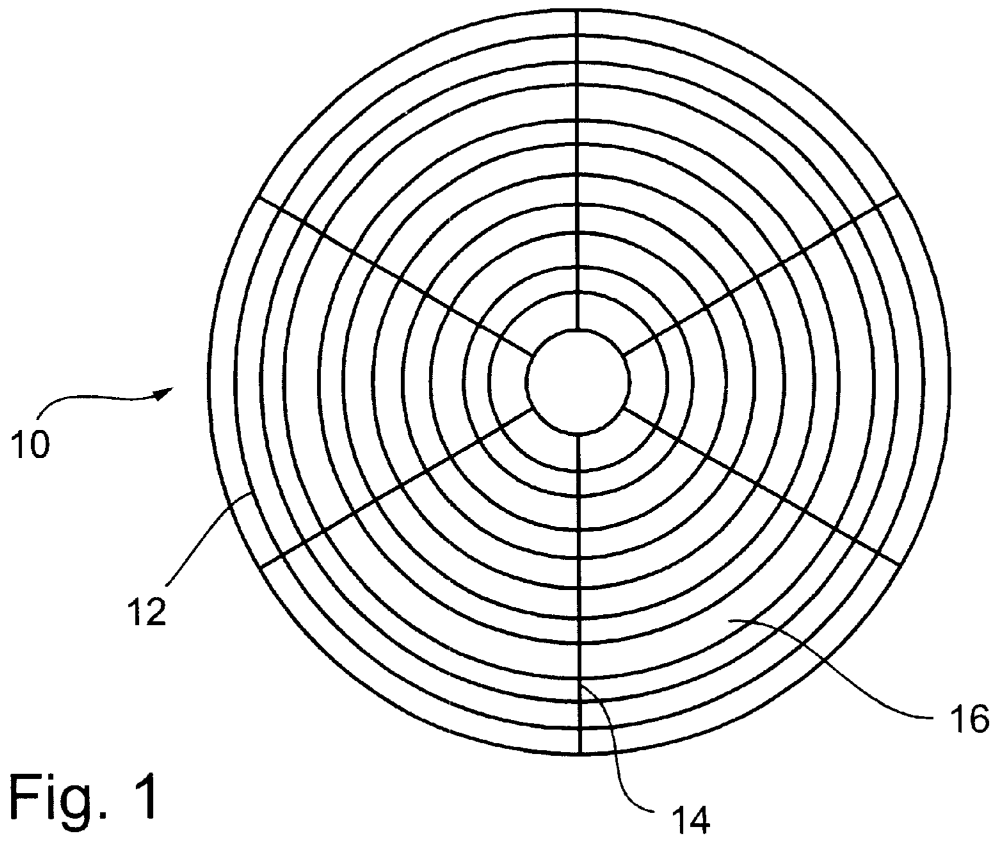
FIG. 1 is a top view of an exemplary spherical cap transducer comprising a plurality of transducer elements to be driven in a phased array.
Figure 2:
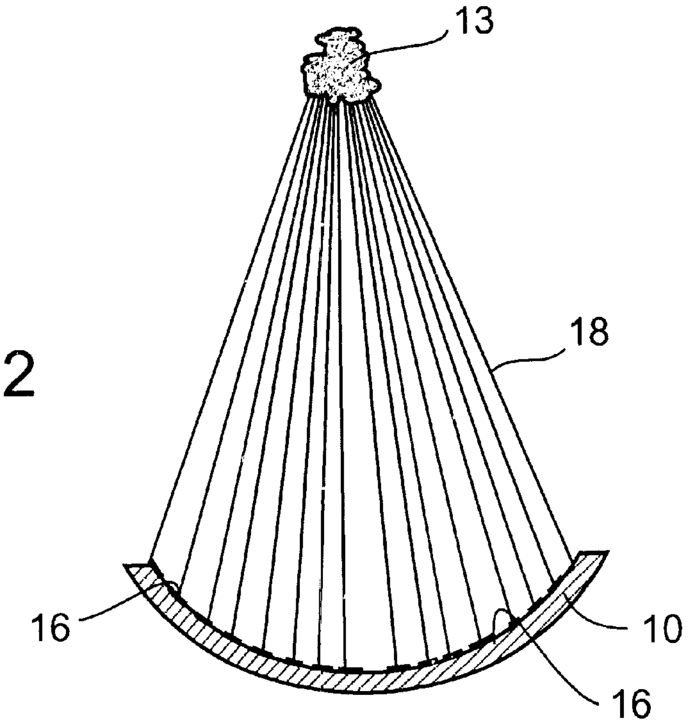
FIG. 2 is a partially cut-away side view of the transducer of FIG. 1, illustrating the concentrated emission of focused ultrasonic energy in a targeted focal region.
Figure 3:
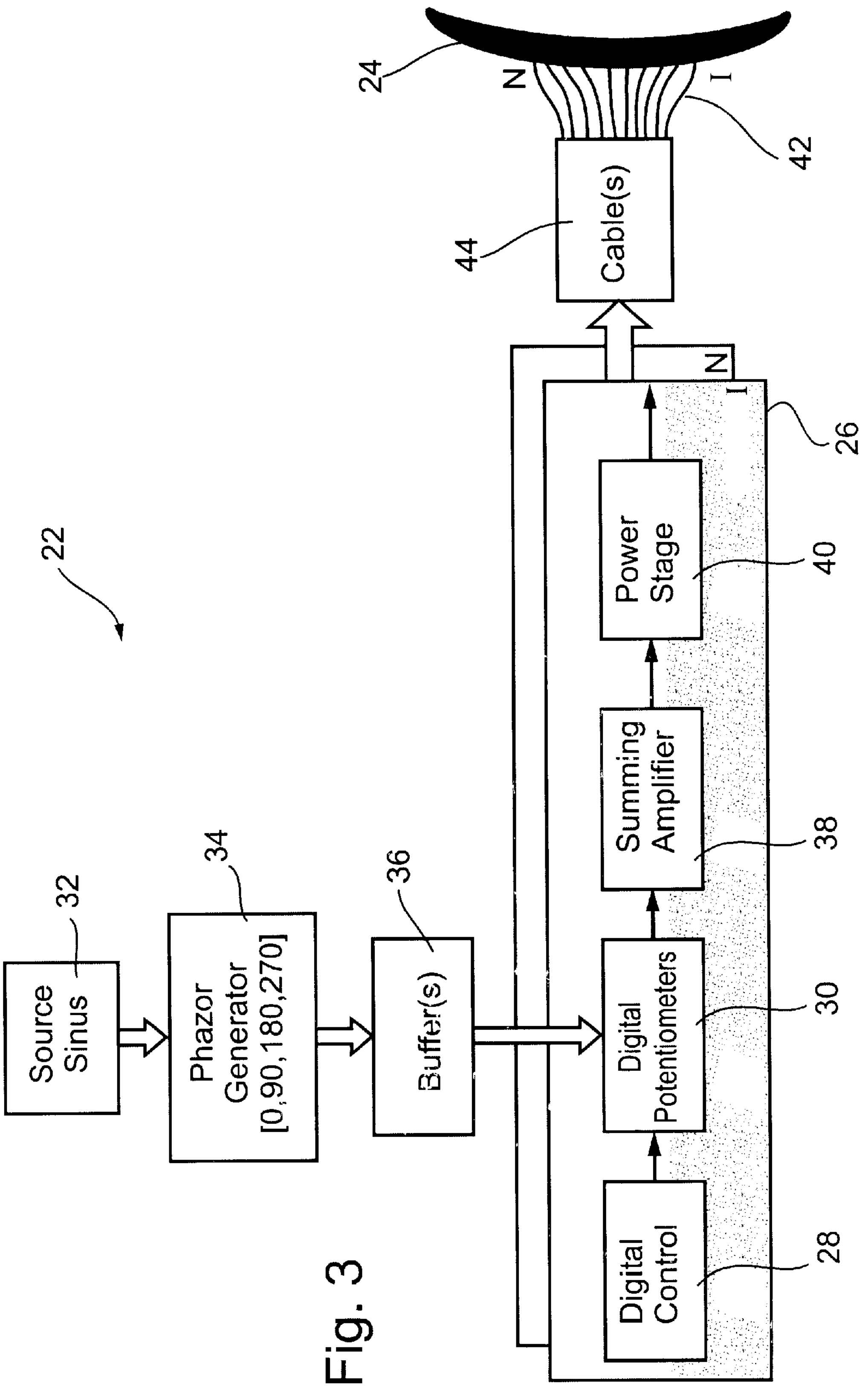
FIG. 3 is a block diagram of a preferred control system for operating a phased array transducer in a focused ultrasound system.

FIG. 3 illustrates a preferred system 22 for driving a phased array transducer 24 in a focused ultrasound system. The transducer 24 has "n" number of individual transducer elements (not shown), each separately driven by a respective sinus wave, $sinus_i$, at the same frequency, although shifted in phase and/or controlled amplitude. In particular, the control system 22 allows for the phase and amplitude of the ultrasonic energy wave emitted from each transducer element to be individually controlled. In alternate embodiments, two or more transducer elements may be driven by the same sinus drive signal, and transducer elements within the array may be driven at differing frequencies. Also, there is no requirement for the transducer to have a particular geometric shape, e.g., it may be a spherical cap, linear array, or other shape.

The sinus waves for driving all transducer elements of transducer 24 are preferably derived from a single source sinus 32 in a manner providing a pure signal, i.e., low distortion, low noise, to avoid signal interference with the imaging modality (e.g., MRI) of the focused ultrasound system. In a preferred embodiment, the source sinus 32 is generated from a direct digital synthesizer, whereby the frequency may be readily changed between a wide range of output frequencies. A phazor generator 34 generates a plurality of "base" sinus waves from the source sinus 32. In the illustrated control system 22, the phazor generator 34 produces four base sinus waves, each offset in phase by exactly 90°, i.e., the base sinuses having respective phases of 0°, 90°, 180° and 270°. As will be appreciated from the entirety of this disclosure, as few as three base sinuses may be generated in alternate embodiments to carry out the invention disclosed herein. In other alternate embodiments, less than four, or more than four base sinuses may be employed. By way of non-limiting examples, three base sinuses, 120° degrees offset from each other, six base sinuses, 60° degrees offset from each other, or eight base sinuses, 45° degress offset from each other may be used. The number and corresponding phase offset of the base sinuses may be varied according to the design choice of one of ordinary skill in the art without departing from the inventive concepts taught herein.

The base sinuses are passed through buffers 36 and distributed to each of"n" control channels 26, which generate the respective sinus drive signals therefrom for each of the n transducer elements of transducer 24. As an alternative design to the 90° linear phase shift from a 0° referece signal, it is possible to use two DDS devices to generate 0° and 90° reference signals, followed by simple inverters to generate all four basic reference sinuses 0°, 90°, 180° (the inverse of 0°) and 270° (the inverse of 90°). In particular, each control channel 26 receives instructions in the form of digital control signals 28 from a central controller composed of a digital hardware circuit (e.g., that can be implemented on a FPGA, CPLD or ASIC) or processor (not shown) for controlling the phase and amplitude of the respective $sinus_i$ to be generated. Another controller (not shown) controls the output frequency of the source sinus 32. The digital control signals 28 contain respective input parameters for a plurality of digitally controlled potentiometers 30 located in each control channel 26. As described in greater detail below, the digital potentiometers precisely scale the amplitudes of each of the base sinuses according to resistance values contained in the respective input parameters.

The scaled sinuses are then passed through a summing amplifier 38 to generate a respective drive sinus having a specifically constructed phase shift and amplitude. The generated drive sinus is passed through an amplification stage 40 to boost the signal to a desired level for driving the respective transducer element. The amplified sinus waves from the control channels 26 are carried over respective wires 42 bundled into one or more transmission cables 44. At the transducer 24, the wires 42 are unbundled and electrically connected to the respective transducer elements in accordance with known wire-transducer bonding techniques.

Figure 4:
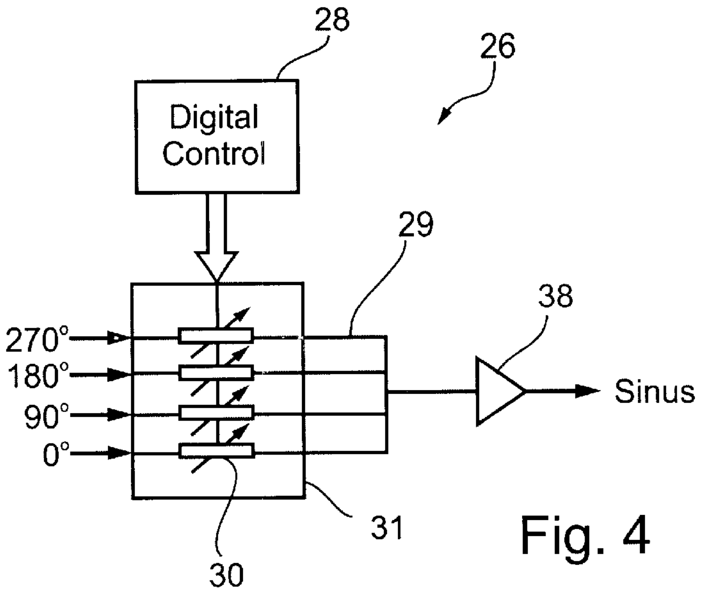
FIG. 4 is a schematic diagram of one preferred circuit embodiment for generating a respective transducer element sinus wave in the system of FIG. 3.

By way of more detailed illustration, FIG. 4 shows one preferred embodiment, wherein a component 31 having four digital potentiometers 30, e.g., such as Analog Devices model AD8403, is provided in each control channel 26. The four base sinuses (0°, 90°, 180°, and 270°) are input into respective potentiometers 30 in the component 31. The input parameters (i.e., potentiometer resistance values) from the respective digital control signal 28 are also input into the respective potentiometers 30. Based on the input parameters, two of the base sinuses are scaled completely to zero, with the amplitude of each of a remaining two (orthogonal) base sinuses respectively scaled to a level determined by the digital input parameters. In particular, the two bases sinuses nearest to the particular phase angle of the $sinus_i$ to be generated are used, while the other two bases sinuses are not needed. The "scaled" base sinuses 29 are then linearly combined by the summing amplifier 38 to produce the respective $sinus_i$.

It will be appreciated that the use of digital potentiometers 30 to scale the base sinuses allows for digitally controlled switching between respective distances, shapes and/or orientations of a focal zone (referred to generally herein as "focal zone characteristics") of the transducer 24. For example, with the use of field programmable gate arrays (FPGA), the respective input parameters for any number of possible focal zone characteristics may be stored in a comprehensive table or memory. The parameters are transffered using digital control signals 28 to the respective control channels 26. Switching between such focal zone characteristics is accomplished in $\mu$ seconds by transmitting a different set of stored digital control signals 28 to the respective control channels 26. Changes in the source sinus frequency (with or without different sets of associated control parameters) may also be rapidly implemented.

Towards this end, sequential changes in the transducer focal zone characteristics may be implemented in the form of sequential sets of digital control signals 28 from the central controller to the respective control channels 26, separated by a time-domain function as part of a single thermal dose or "sonication." In other words, during a single sonication, the system 22 has the ability to switch between ultrasound energy beam shapes at a rate that is relatively high compared to the heat transfer time constant in a patient's tissue. This ability is achieved by performing several "sub-sonications" during one sonication.

By way of example, a sonication of ten seconds in duration may include changing the output frequency every second (e.g., changing back and forth between two frequencies to reduce secondary hot spots), while independently changing the respective transducer focal zone characteristics every 0.25 seconds. The transitions every 0.25 seconds between sub-sonications are preferably performed with minimal line oscillations, and without intervention by the central controller. A system for optimizing sonication parameters for a focused ultrasound system is disclosed in U.S. patent application Ser. No. 09/724,670, entitled "METHOD AND APPARATUS FOR CONTROLLING THERMAL DOSING IN AN Thermal treatment SYSTEM" and filed on Nov. 28, 2000, which is hereby incorporated by reference.

Figure 5:
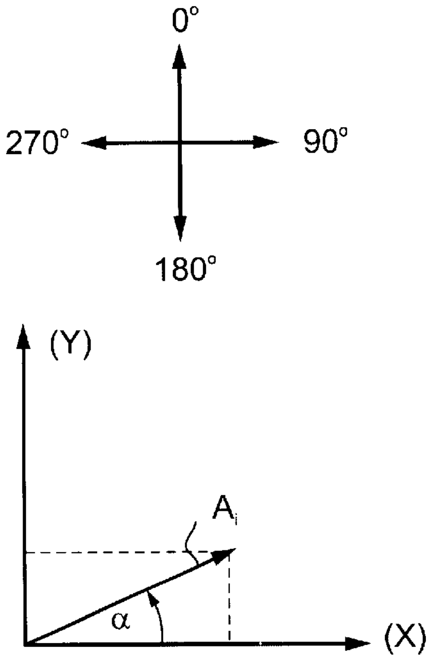
FIG. 5 illustrates a vector in a complex plane for representing a sinus wave.

In accordance with a general concept employed by the control system 22, the particular scaling and linear combination of the base sinuses in each control channel 26 and, thus, the phase and amplitude of the particular generated $sinus_i$, are determined as follows:

A given sinus wave "i" has both real and imaginary components that can be represented as a vector in a complex plane as $A_i\cos(\omega t+\alpha)$, where A is the amplitude, $\omega$ is the frequency and $\alpha$ is the phase of the sinus wave i. This vector $A_i$ is graphically represented in X-Y coordinates in FIG. 5 as $A_i\angle\alpha_{imag}$. With reference still to FIG. 5, vector $A_i$ may also be expressed as a sum of the two base sinus vectors 0° ($K_1$*Y) and 90° ($K_2$*X) according to the expression $A_i=K_1*Y+K_2*X$, where $K_1$ and $K_2$ are the amplitudes of the 0° and 90° base sinuses constants. Thus, by precisely scaling the amplitudes of the respective base sinus waves, a resulting $sinus_i$ of any phase between 0° and 90° may be derived by adding the two scaled base sinuses together. From this, it is possible to generate any sum vector from 0° to 360° in any desired amplitude.

Figure 6:
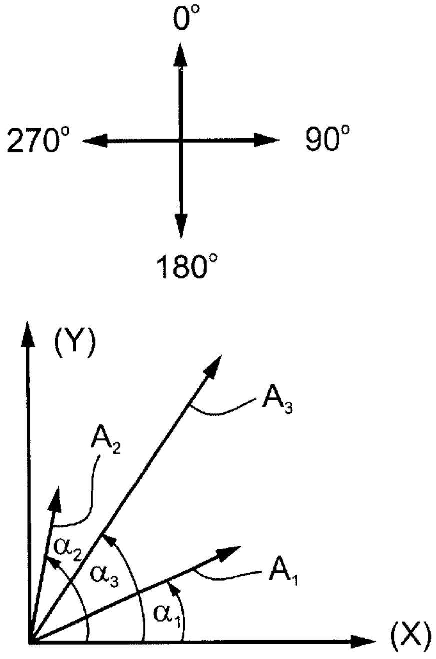
FIG. 6 illustrates the adding of first and second sinus vectors to generate a third sinus vector.
Figure 7A:
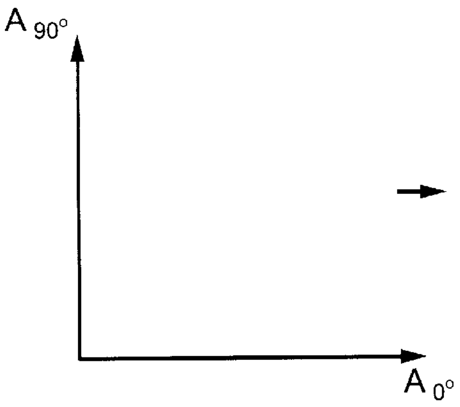
FIGS. 7(*a*)–(*d*) illustrate generation of variously phased sinus vectors in the system of FIG. 3.
Figure 7B:
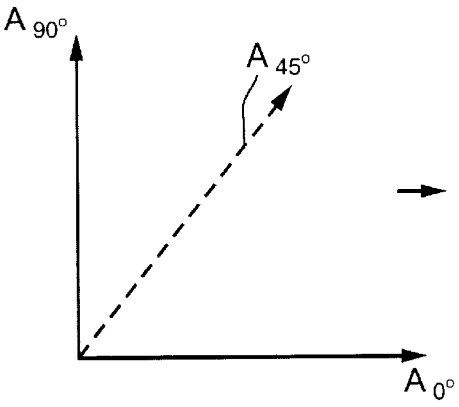
Figure 7C:
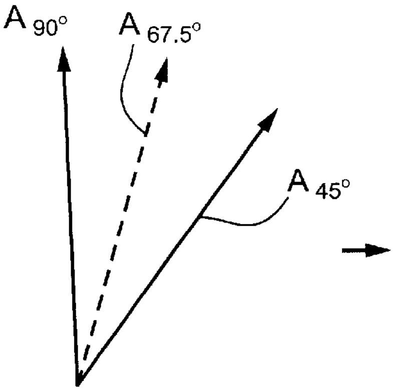
Figure 7D:
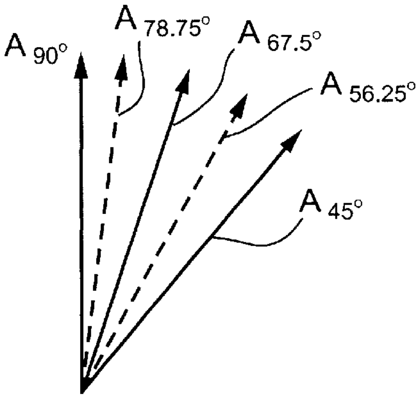

Similarly, with reference to FIG. 6, it is possible to add, or sum, a first sinus vector $A_1$ with a second sinus vector $A_2$ to generate a third sinus vector $A_3$, according to the relationship $A_1\cos(\omega t+\alpha_1)+A_2\cos(\omega t+\alpha_2)=A_3\cos(\omega t+\alpha_3)$, so long as the angle $\alpha_3$ is between the respective angles $\alpha_1$ and $\alpha_2$. As such, a sinus vector of any given phase angle $\alpha_i$ may be generated from the base sinus waves at 0°, 90°, 180°, 270°. As will be observed, a sinus of any phase can be generated from as few as three base sinuses, e.g., 0°, 120° and 240°, so long as the three base sinuses are separated in phase from each other by at least 90°. It will be further appreciated that a greater number of base sinus waves may also be employed, e.g., 0°, 45°, 90°, 135°, 180°, 225°, 270° and 315°.

By way of further illustration, FIGS. 7(*a*)–(*d*) show the generation of various sinus vectors $A\angle_{78.75°}$, $A\angle_{67.5°}$, $A\angle_{56.25°}$ and $A\angle_{45°}$ from base sinus vectors $A\angle_{90°}$, $A\angle_{0°}$. In particular, sinus vector $A\angle_{45°}$ is generated by scaling and summing base sinus vectors $A\angle_{90°}$ and $A\angle_{0°}$. In this instance, the 180° and 270° base sinus waves will be scaled to zero by the respective digital potentiometers 30. The sinus vector $A\angle_{67.5°}$ is generated by scaling and summing base sinus vector $A_{90°}$ with sinus vector $A\angle_{45°}$. Sinus vector $A\angle_{78.75°}$ is generated by scaling and summing base sinus vector $A\angle_{90°}$ with sinus vector $A\angle_{67.5°}$. Sinus vector $A\angle_{56.25°}$ is generated by scaling and summing sinus vector $A\angle_{67.5°}$ with sinus vector $A\angle_{45°}$.

Figure 8:
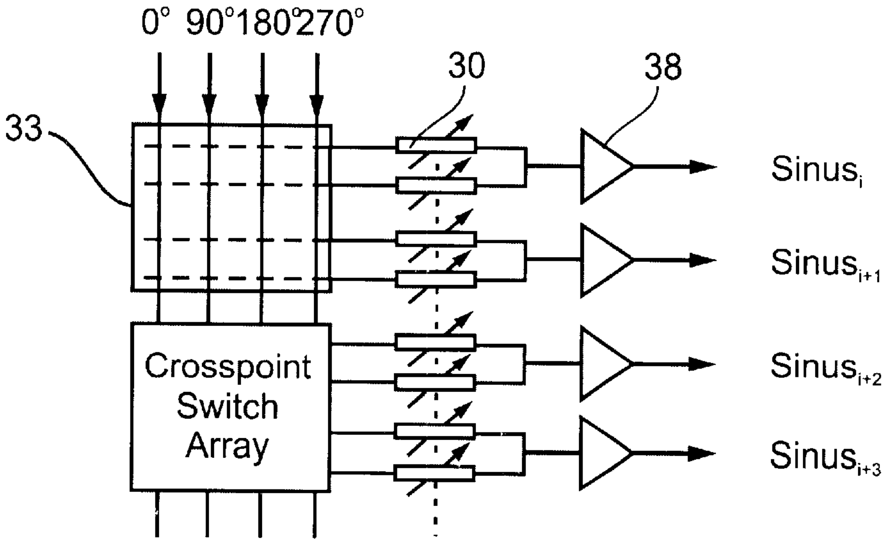
FIG. 8 is a schematic diagram of another preferred circuit embodiment for generating a respective transducer element sinus wave in the system of FIG. 3.

FIG. 8 shows an alternate embodiment of the system 22, wherein a plurality of cross-point switch arrays 33 are used to reduce the overall number of digital potentiometers 30 needed. In particular, a four-by-four cross-point switch array 33, such as, e.g., Analog Devices model AD8108 receives the four base sinuses (0°, 90°, 180°, and 270°). One or more parameter fields in the digital control signals 28 are input into the respective cross-point switch array 33 and cause the array to isolate and pass through the respective two base sinuses needed to generate the particular channel $sinus_i$ to a pair of potentiometers 30. As will be appreciated by those skilled in the art, other cross-point switch array types and sizes may be used for isolating the respective base sinus pairs needed in one or more control channels 26. Notably, each channel 26 must include at least two digital potentiometers 30 to determine both the phase and amplitude of the respective $sinus_i$.

Figure 9:
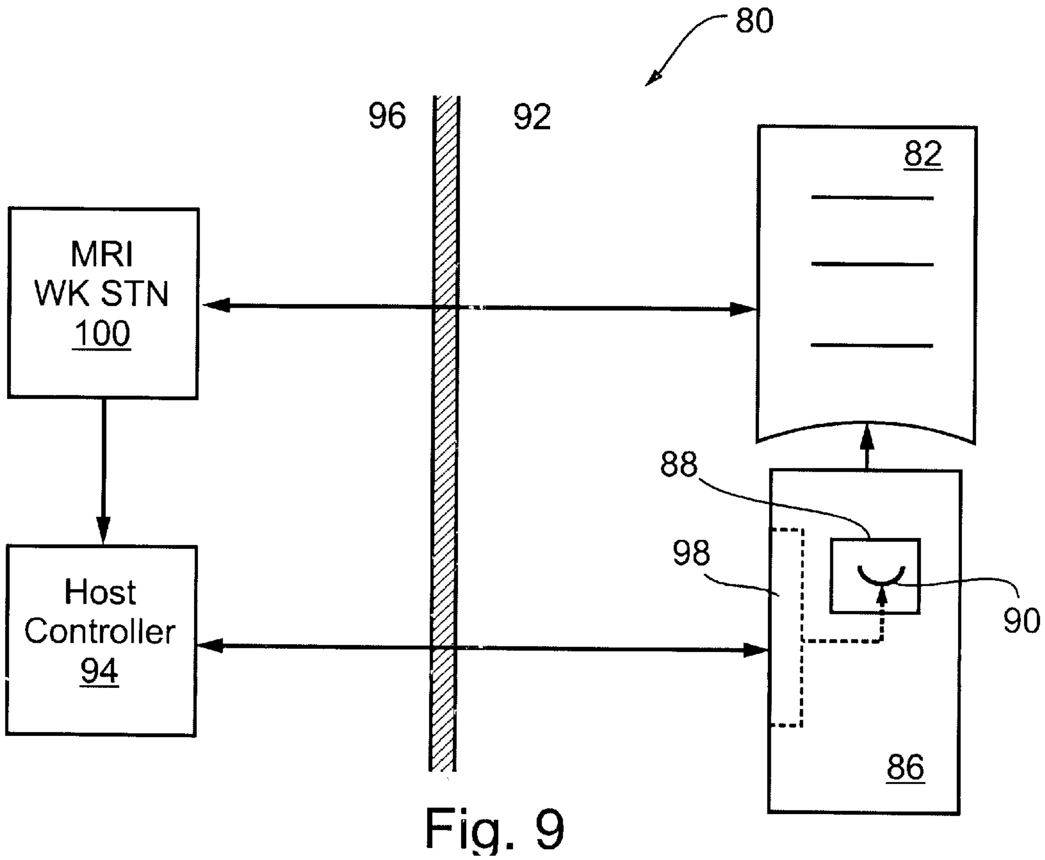
FIG. 9 is a block diagram of an exemplary MRI-guided focused ultrasound system.

For purposes of better understanding the inventive concepts described herein, FIG. 9 depicts an exemplary MRI-guided focused ultrasound system 80. The system 80 generally comprises a MRI machine 82 having a cylindrical chamber for accommodating a patient table 86. A sealed water bath 88 is embedded in (or otherwise located atop) the patient table 86 in a location suitable for accessing a target tissue region to be treated in a patient lying on the table 86. Located in the water bath 88 is a movable phased-array transducer 90 having "n" transducer elements. The transducer 90 preferably has a spherical cap shape similar to transducer 24 of FIG. 3. Specific details of a preferred transducer positioning system for controlling the position along x and y coordinates, as well as the pitch, roll and yaw, of the transducer 90 are disclosed in U.S. patent application Ser. No. 09/628,964, filed Jul. 31, 2000, and entitled, "Mechanical Positioner For MRI Guided Ultrasound Therapy System," which is hereby incorporated by reference. General details of MRI-guided focused ultrasound systems are provided in U.S. Pat. Nos. 5,247,935, 5,291,890, 5,323,779 and 5,769,790, which are also hereby incorporated by reference.

The MRI machine 82 and patient table 86 are located in a shielded MRI room 92. A host control computer ("host controller") 94 is located in an adjacent equipment room 96, so as to not interfere with the operation of the MRI machine 82 (and vice versa). The host controller 94 communicates with a transducer beam control system ("transducer controller") 98, which is preferably attached about the lower periphery of the patient table 86 so as to not otherwise interfere with operation of the MRI machine 82. Collectively, the host controller 94 and transducer beam control system 98 perform the functions of the above-described control system 22. In particular, the host controller 94 provides the sonication parameters to the transducer control system 98 for each patient treatment session performed by the system 80. Each patient treatment session will typically include a series of sonications, e.g., with each sonication lasting approximately ten seconds, with a cooling period of, e.g., approximately ninety seconds, between each sonication. Each sonication it self will typically comprise a plurality of subsonications, e.g., of approximately one-two seconds each, wherein the frequency and/or focal zone characteristics may vary with each subsonication. The sonication parameters provided from the host controller 94 to the transducer controller 98 include the digital control parameters for setting the phase offset and amplitude for the drive sinus wave for each transducer element of the transducer 90 for each subsonication period.

Also located in the equipment room 96 is a MRI work station 100 on which MR images of the treatment area within the patient are presented to an attending physician or technician overseeing the treatment session. As taught in the above-incorporated U.S. patent application Ser. No. 09/724,670, the MRI work station 100 preferably provides feedback images to the host controller 94 of the real time tissue temperature changes in the target tissue region of a patient during a sonication. The host controller 94 may adjust the sonication parameters for the ensuing sonication(s) of a treatment session based on the feedback images.

Figure 10:
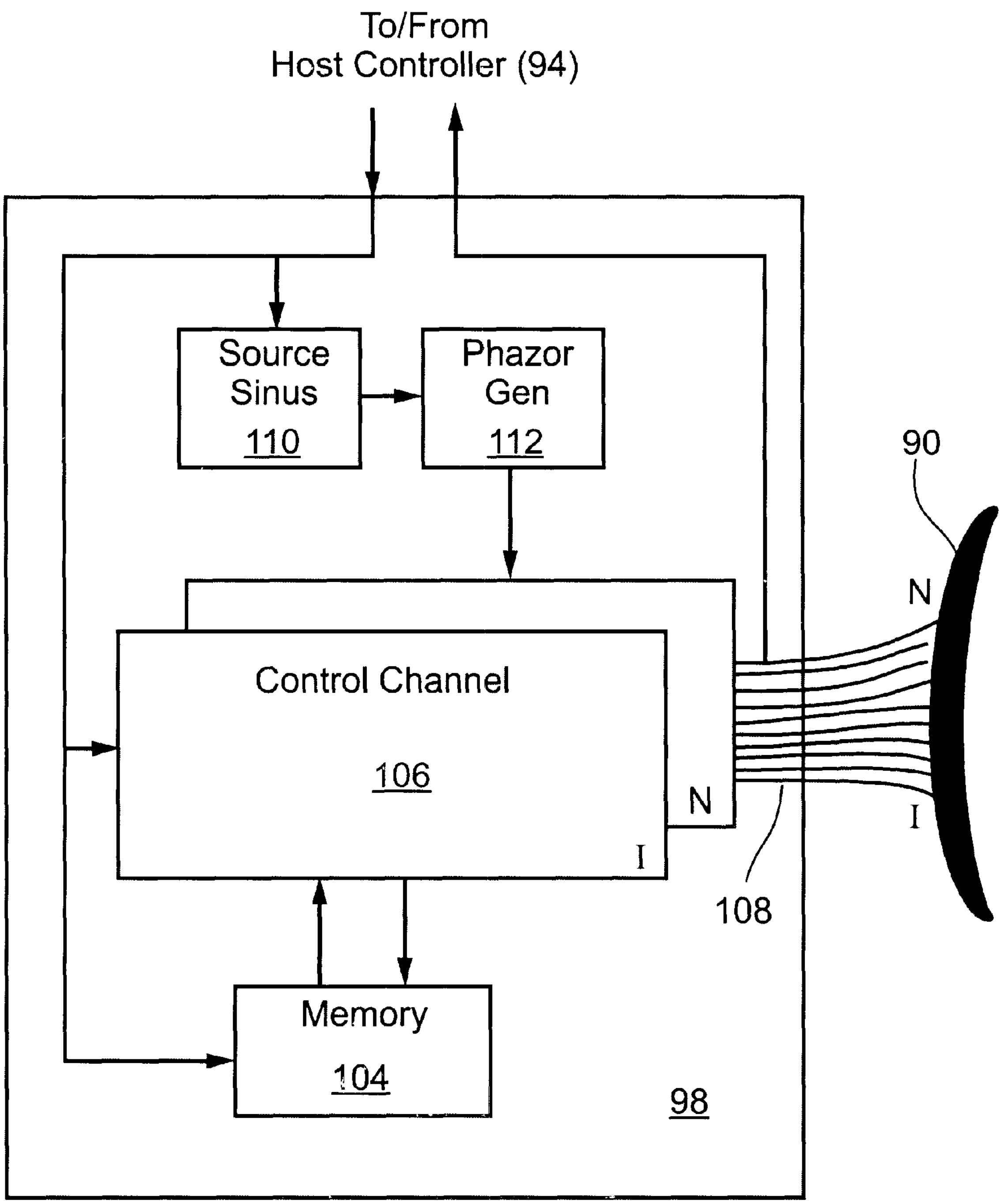
FIG. 10 is a block diagram of a preferred control system for operating a phased array transducer in the focused ultrasound system of FIG. 9.

Referring to FIG. 10, before each treatment session begins, and then during the cooling period following each sonication, the transducer controller 98 receives the sonication parameters for the ensuing sonication from the host controller 94 and stores them in a memory 104. At the initiation of the sonication, the parameters are input into n respective control channels 106 for generating n sinus drive waves 108 from a source sinus generator 110 and phazor generator 112, respectively, for driving the n transducer elements of transducer 90.

The host controller 94 is also preferably configured to oversee patient safety during each sonication, by monitoring the actual output phase and amplitude of the respective $sinus_i$ drive signals and then comparing the actual values to a corresponding set of expected, or planned, output levels for the respective sonication parameters. In one embodiment, this is accomplished by a low noise multiplexing of the (fully amplified) sinus drive waves 108 to an A/D board in the host controller 94, where the measurements are taken. If the actual phase or amplitude differs from what is expected for the respective $sinus_i$, the particular drive sinus wave 108, or perhaps the entire system 80, may be shut down as a precautionary safety measure.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed:

1. A focused ultrasound system, comprising:

a sinus source configured to generate a sinus signal;

a phazor generator coupled to said sinus source and configured to generate a plurality of base waves in response to the sinus signal;

a plurality of control channels coupled to said phazor generator and configure to generate a plurality of drive signals in response to the plurality of base waves, each of said plurality of control channels controlling a relative phase shift, an amplitude, or both, of a corresponding one of the plurality of drive signals; and a transducer array having a plurality of transducer elements coupled to said plurality of control channels and configured to emit an acoustic energy beam in response to the plurality of drive signals.

2. The system of claim 1, further comprising a controller coupled to said plurality of control channels for providing input parameters to control the relative phase shift, the amplitude, or both, of each of the plurality of drive signals for determining a distance, shape, orientation, or any combination thereof, of a focal zone of the acoustic energy beam.

3. The system of claim 1, further comprising a controller coupled to said plurality of control channels for providing input parameters corresponding to a set of expected phase shifts, amplitudes, or both, during a sonication, monitoring a set of actual phase shifts, amplitudes, or both, during the sonication, and comparing the set of actual phase shifts, amplitudes, or both to the set of expected phase shifts, amplitudes, or both.

4. The system of claim 3, wherein the controller is further configured to shut down one or more of the plurality of drive signals in response to the set of actual phase shifts, amplitudes, or both, sufficiently varying from the set of expected phase shifts, amplitudes, or both.

5. The system of claim 1, wherein each of said plurality of control channels comprises:

a digital controller; and a plurality of digital potentiometers, each having a first input coupled to said digital controller, a second input coupled to said phazor generator, and an output coupled to said transducer array.

6. The system of claim 5, wherein each of said plurality of control channels further comprises a sampling amplifier coupled between said plurality of digital potentiometers and said transducer array.

7. The system of claim 5, wherein each of said plurality of control channels further comprises a cross point switch array coupled between said phazor generator and said plurality of digital potentiometers.

8. The system of claim 5, wherein said plurality of digital potentiometers scale the plurality of base waves in response to a control signal from said digital controller.

9. The system of claim 5, wherein said digital controller is configured to provide a plurality of successive sonication parameters to vary a distance, shape, orientation, or any combination thereof, of a focal zone of the acoustic energy beam.

10. The system of claim 9, wherein a frequency of the plurality of drive signals is determined in accordance with the plurality of successive sonication parameters provided to the sinus source.

11. The system of claim 1, wherein said phazor generator produces four base waves having relative phases of approximately 0°, 90°, 180°, and 270°.

12. The system of claim 1, wherein said phazor generator produces three base waves having relative phases of approximately 0°, 120°, and 240°.

13. The system of claim 1, wherein said phazor generator produces six base waves having relative phases of approximately 0°, 60°, 120°, 180°, 240°, and 300°.

14. The system of claim 1, wherein said phazor generator produces eight base waves having relative phases of approximately 0°, 45°, 90°, 135°, 180°, 225°, 270°, and 315°.

15. A focused ultrasound system, comprising:

a transducer having a plurality of transducer elements for emitting acoustic energy;

a sinus generator for producing a source sinus wave;

phazor generation circuitry for producing a plurality of base sinus waves from the source sinus wave, the base sinus waves being offset in phase from one another; and a plurality of control channels, each control channel associated with a respective transducer element, each control channel receiving as inputs the base sinus waves, each control channel having a plurality of digitally controlled elements configured for scaling selected ones of the input base sinus waves, each control channel having summing circuitry for summing the respective scaled input base sinus waves to produce a drive sinus wave for driving the respective transducer element.

16. The system of claim 15, further comprising a controller providing control parameters to the respective control channels to thereby control a relative phase shift, amplitude, or both, of the respective drive sinus waves in order to determine a distance, shape, orientation, or any combination thereof, of a focal zone of acoustic energy emitted by the transducer elements.

17. The system of claim 16, wherein the sinus generator is configured to change the frequency of the source sinus, thereby changing the frequency of the respective drive sinus waves, based on input parameters received from the controller.

18. The system of claim 15, wherein the phazor generation circuitry produces four base sinus waves from the source sinus wave, the base sinus waves having relative phases of approximately 0°, 90°, 180°, and 270°.

19. The system of claim 18, wherein the phazor generation circuitry produces eight base sinus waves from the source sinus wave, the base sinus waves having relative phases of approximately 0°, 45°, 90°, 135°, 180°, 225°, 270° and 315°.

20. The system of claim 15, wherein the phazor generation circuitry produces three base sinus waves from the source sinus wave, the base sinus waves having relative phases of approximately 0°, 120° and 240°.

21. The system of claim 15, wherein the phazor generation circuitry produces six base sinus waves from the source sinus wave, the base sinus waves having relative phases of approximately 0°, 60°, 120°, 180°, 240° and 300°.

22. In a focused ultrasound system having a plurality of transducer elements driven by a corresponding plurality of sinus drive signals to thereby emit acoustic energy, a method for generating respective sinus drive signals having a relative phase shift, amplitude, or both, comprising:

providing a source sinus wave;

generating a plurality of base sinus waves from the source sinus wave, the base sinus waves being offset in phase from one another;

scaling the amplitude of a first base sinus wave to produce a first scaled sinus wave;

scaling the amplitude of a second base sinus wave to produce a second scaled sinus wave; and summing the first and second scaled sinus waves to generate a respective drive signal.

23. The method of claim 22, wherein the first and second base sinus waves are scaled using digitally controlled elements.

24. The method of claim 22, further comprising comparing an expected phase shift, amplitude, or both, of a transducer element driven by the respective drive signal to an actual phase shift, amplitude, or both, of the transducer element during a sonication.

25. The method of claim 24, further comprising turning off the drive signal if the actual phase shift, amplitude, or both, of the transducer element sufficiently varies from the expected phase shift, amplitude, or both.

* * * * *